United States Patent
Frater et al.

(10) Patent No.: US 10,427,146 B2
(45) Date of Patent: Oct. 1, 2019

(54) IMMOBILIZED METATHESIS TUNGSTEN OXO ALKYLIDENE CATALYSTS AND USE THEREOF IN OLEFIN METATHESIS

(71) Applicant: XiMo AG, Horw/Lucerne (CH)

(72) Inventors: Georg Emil Frater, Ebnat-Kappel (CH); Jeno Varga, Horw/Lucerne (CH); Christophe Coperet, Zurich (CH); Victor Mougel, Zurich (CH); Matthew P. Conley, Zurich (CH)

(73) Assignee: XiMo AG, Horw/Lucerne (CH)

( * ) Notice: Subject to any disclaimer, the term of this patent is extended or adjusted under 35 U.S.C. 154(b) by 0 days.

(21) Appl. No.: 15/023,892

(22) PCT Filed: Sep. 30, 2014

(86) PCT No.: PCT/EP2014/002654
§ 371 (c)(1),
(2) Date: Mar. 22, 2016

(87) PCT Pub. No.: WO2015/049047
PCT Pub. Date: Apr. 9, 2015

(65) Prior Publication Data
US 2016/0236185 A1    Aug. 18, 2016

(30) Foreign Application Priority Data
Oct. 1, 2013 (EP) .................................... 13004732

(51) Int. Cl.
| B01J 31/22 | (2006.01) |
| B01J 31/16 | (2006.01) |
| B01J 31/18 | (2006.01) |
| C07C 6/04 | (2006.01) |
| C07C 67/475 | (2006.01) |
| C07C 67/30 | (2006.01) |
| C07F 11/00 | (2006.01) |
| C08G 61/08 | (2006.01) |

(52) U.S. Cl.
CPC ....... *B01J 31/2265* (2013.01); *B01J 31/1608* (2013.01); *B01J 31/181* (2013.01); *B01J 31/1805* (2013.01); *B01J 31/2208* (2013.01); *B01J 31/2226* (2013.01); *C07C 6/04* (2013.01); *C07C 67/30* (2013.01); *C07C 67/475* (2013.01); *C07F 11/00* (2013.01); *B01J 2231/543* (2013.01); *B01J 2531/66* (2013.01); *C07C 2531/22* (2013.01); *C08G 61/08* (2013.01); *C08G 2261/418* (2013.01); *C08G 2261/419* (2013.01)

(58) Field of Classification Search
CPC .................................................. B01J 31/2265
See application file for complete search history.

(56) References Cited

U.S. PATENT DOCUMENTS

| 3,400,170 | A | 9/1968 | Presswood et al. |
| 3,696,161 | A | 1/1972 | Kobetz et al. |
| 3,647,913 | A | 3/1972 | Lasis |
| 3,689,584 | A | 9/1972 | Kobetz |
| 4,637,197 | A | 1/1987 | Banfield et al. |
| 5,210,365 | A | 5/1993 | Lin |
| 5,378,783 | A | 1/1995 | Okumura et al. |
| 6,121,473 | A | 9/2000 | Schrock et al. |
| 8,222,469 | B2 | 7/2012 | Schrock et al. |
| 8,642,824 | B2 | 2/2014 | Lemke et al. |
| 8,692,006 | B2 | 8/2014 | Uptain et al. |
| 8,957,268 | B2 | 2/2015 | Cohen et al. |
| 8,993,470 | B2 | 3/2015 | Fuerstner et al. |
| 9,079,173 | B2 | 7/2015 | Schrock et al. |
| 9,216,941 | B2 | 12/2015 | Lemke et al. |
| 9,284,515 | B2 | 3/2016 | Uptain et al. |
| 9,328,055 | B2 | 5/2016 | Balakrishnan et al. |
| 9,388,097 | B2 | 7/2016 | Wampler et al. |

(Continued)

FOREIGN PATENT DOCUMENTS

| EP | 0116408 | 1/1984 |
| EP | 0534388 | 3/1993 |
| EP | 0864595 | 9/1998 |
| EP | 2703081 | 3/2014 |
| JP | 2013014562 | 5/2016 |
| WO | 2008066754 | 6/2008 |
| WO | 2009020665 | 2/2009 |
| WO | 2009020667 | 2/2009 |
| WO | 2009094201 | 7/2009 |
| WO | 2011007742 | 1/2011 |

(Continued)

OTHER PUBLICATIONS

Blanc, et al. "Direct Observation of Reaction Intermediates for a Well Defined Heterogeneous Alkene Metathesis Catalyst", PNAS, vol. 105 No. 34, Aug. 26, 2008, pp. 12123-12127.

(Continued)

*Primary Examiner* — Joseph R Kosack
(74) *Attorney, Agent, or Firm* — Stoel Rives LLP

(57) ABSTRACT

Method of making an immobilized tungsten catalyst comprising or consisting of $(\equiv SiO)_X$ $W(=O)(=CR^1R^2)(R^3$ or $R^4)_{2-X}(L)_z$, comprising at least the following step (i): (i) reacting silica (SiO2) with a tungsten oxo alkylidene complex comprising or consisting of $(R^3)(R^4)W(=O)(=CR^1R^2)(L)_y$, preferably wherein $=CR^1R^2$ is selected from $=CHC(CH_3)_3$ or $=CH(C(CH_3)_2)C_6H_5$ and $R^3$ and $R^4$ are independently selected from pyrrol-1-yl, 2,5-dimethylpyrrol-1-yl, or 2,5-diphenylpyrrol-1-yl, or —OR, wherein R is a six membered or 10 membered aryl ring, optionally substituted.

17 Claims, 2 Drawing Sheets

(56) References Cited

U.S. PATENT DOCUMENTS

| | | | |
|---|---|---|---|
| 9,469,827 B2 | 10/2016 | Cohen et al. | |
| 9,687,834 B2 | 6/2017 | Malcolmson et al. | |
| 9,732,282 B2 | 8/2017 | Cohen et al. | |
| 9,776,179 B2 | 10/2017 | Wampler et al. | |
| 9,890,348 B2 | 2/2018 | Cohen | |
| 9,919,299 B2 | 3/2018 | Ondi et al. | |
| 9,944,860 B2 | 4/2018 | Cohen et al. | |
| 2002/0165420 A1 | 11/2002 | Elomari et al. | |
| 2003/0135080 A1 | 7/2003 | Botha et al. | |
| 2004/0260137 A1 | 12/2004 | Elomari et al. | |
| 2005/0107529 A1 | 5/2005 | Datta et al. | |
| 2005/0124839 A1 | 6/2005 | Gartside et al. | |
| 2005/0154221 A1 | 7/2005 | Lysenko et al. | |
| 2008/0119678 A1 | 5/2008 | Hock et al. | |
| 2011/0015430 A1 | 1/2011 | Schrock et al. | |
| 2011/0077421 A1 | 3/2011 | Schrock et al. | |
| 2011/0113679 A1 | 5/2011 | Cohen et al. | |
| 2011/0160472 A1 | 6/2011 | Lemke et al. | |
| 2011/0263917 A1 | 10/2011 | Van Hal et al. | |
| 2012/0316057 A1* | 12/2012 | Taoufik | C07F 11/00 502/155 |
| 2013/0006012 A1 | 1/2013 | Firth et al. | |
| 2013/0035502 A1 | 2/2013 | Cohen et al. | |
| 2013/0144102 A1 | 6/2013 | Fuerstner et al. | |
| 2013/0217906 A1 | 8/2013 | Kunz et al. | |
| 2014/0275595 A1 | 9/2014 | Wampler et al. | |
| 2014/0309466 A1 | 10/2014 | Ondi et al. | |
| 2015/0105566 A1 | 4/2015 | Cohen et al. | |
| 2015/0197683 A1 | 7/2015 | Hategan et al. | |
| 2015/0197711 A1 | 7/2015 | Littich et al. | |
| 2016/0030936 A1 | 2/2016 | Ondi et al. | |
| 2016/0122375 A1 | 5/2016 | Coperet et al. | |
| 2016/0159727 A1 | 6/2016 | Frater et al. | |
| 2016/0236185 A1 | 8/2016 | Frater et al. | |
| 2017/0011038 A1 | 1/2017 | Revelle | |
| 2017/0066972 A1 | 3/2017 | Cohen | |
| 2017/0066993 A1 | 3/2017 | Wampler et al. | |
| 2017/0348681 A1 | 12/2017 | Coperet et al. | |
| 2018/0044597 A1 | 2/2018 | Cohen et al. | |
| 2018/0099268 A1 | 4/2018 | Wampler et al. | |
| 2018/0208873 A1 | 7/2018 | Cohen et al. | |

FOREIGN PATENT DOCUMENTS

| | | |
|---|---|---|
| WO | 2011008258 | 1/2011 |
| WO | 2011046872 | 4/2011 |
| WO | 2011097642 | 8/2011 |
| WO | 2012116695 | 9/2012 |
| WO | 2013192384 | 12/2013 |
| WO | 2014016047 | 1/2014 |
| WO | 2014139679 | 9/2014 |
| WO | 2014150470 | 9/2014 |
| WO | 2014160417 | 10/2014 |
| WO | 2015003815 | 1/2015 |
| WO | 2015108874 | 7/2015 |
| WO | 2015142688 | 9/2015 |
| WO | 2015155593 | 10/2015 |
| WO | 2015162245 | 10/2015 |
| WO | 2017087710 | 5/2017 |
| WO | 2018091664 | 5/2018 |
| WO | 2018138204 | 8/2018 |
| WO | 2018150379 | 8/2018 |

OTHER PUBLICATIONS

Mazoyer, et al., "Development of the First Well-Defined Tungsten Oxo Alkyl Derivatives Supported on Silica by SOMC: towards a Model of WO3/SiO2 Olefin Metathesis Catalyst", Chem. Commun., 46, 2010, 8944-8946.

Merle, et al., "On the Track to Silica-Supported Tungsten Oxo Metathesis Catalysts: Input from O Solid-State NMR", Inorg. Chem., 52, 2013, 10119-10130.

Peryshkov, et al., "Synthesis of Tungsten Oxo Alkylidene Complexes", Organometallics, 31, 2012, 7278-7286.

Peryshkov, et al., "Z-Selective Olefin Metathesis Reactions Promoted by Tungsten Oxo Alkylidene Complexes", JACS, 133, 2011, 20754-20757.

Rhers, et al., "A Well-Defined, Silica-Supported Tungsten Imido Alkylidene Olefin Metathesis Catalyst", Organometallics, 25, 2006, 3554-3557.

Office Action dated Feb. 10, 2017 for U.S. Appl. No. 14/209,313.

Blanc, et al., "Dramatic Improvements of Well-Defined Silica Supported Mo-Based Olefin Metathesis Catalysts by Tuning the N-Containing Ligands", J Am Chem Soc., 129(27), 2007, 8434-8435.

Blanc, et al., "Highly Active, Stable, and Selective Well-Defined Silica Supported Mo Imido Olefin Metathesis Catalysts", J Am Chem Soc., 129(17), 2007, 1044-1045.

Office Action dated Mar. 24, 2017 for U.S. Appl. No. 14/774,404.

PCT/EP2014/002654, International Search Report and Written Opinion, dated Dec. 17, 2014, 10 pages.

Office Action dated Aug. 24, 2017 for U.S. Appl. No. 14/209,313.

Blanc, et al.,Surface versus Molecular Siloxy Ligands in Well-Defined Olefin Metathesis Catalysts: [{(RO)3SiO}Mo(=NAr)(=CHtBu)(CH2tBu)], Angew. Chem. Int. Ed. 2007, 45, 1216-1220.

Chabanas, et al.,A Highly Active Well-Defined Rhenium Heterogenous Catalyst for Olefin Metathesis Prepared via Surface Organometallic Chemsitry, J. Am Chem Soc. 2001, 123, 2062-2063.

Frater, et al., Office Action dated Jun. 9, 2017 for U.S. Appl. No. 14/903,119.

Jiang, et al.,Highly Z-Selective Metathesis Homocoupling of Terminal Olefins, J Am Chem Soc., 131(46) ,2009 ,16630-16631.

Malcolmson, et al.,Highly Efficient Molybdenum-Based Catalyst for Enantioselective Alkene Metathesis, Nature, 456(7224), Epub Nov. 16, 2008 ,Dec. 18, 2008 ,933-937.

Solans-Monfort, et al.,d0 Based Olefin Metathesis Catalysts, Re(=CR)(=CHR)(X)(Y): The Key Role of X and Y Ligands for Efficient Active Sites, J. Am. Chem. Soc. 2005, 127 14015-14025.

Wang, et al.,Molybdenum-Based Complexes with Two Aryloxides and a Pentafluoroimido Ligand: Catalysts for Efficient Z-Selective Synthesis of a Macrocyclic Trisubstituted alkene by Ring-Closing Metathesis, Angew Chem Int Ed Engl, 52(7) 2013 ,1939-1943.

Notice of Allowance dated Nov. 2, 2017 for U.S. Appl. No. 14/774,404.

Office Action dated Jan. 11, 2018 for U.S. Appl. No. 14/903,119.

Jarupatrakorn, et al.,Synthesis and Characterization of MO[OSitBu)3]4 and MO2[OSi(OtBu)3]2 (M=Mo, W): Models for Isolated Oxo-Molybdenum and -Tungsten Sites on Silica and Precursors to Molybdena- and Tungsta-Silica Materials, Chem. Mater. 17 2005 ,1818-1828.

Marciniec, et al.,Metathetical Activity of Allylsubstituted Silanes in the Presence of Ruthenium Catalyst, Journal of Molecular Catalysis, 90 ,1994 ,125-133.

Saito, et al.,1,4-Bis(trimethylsilyl)-1,4-diaza-2,5-cyclohexadienes as Strong Salt-Free Reductants for Generating Low-Valent Early Transition Metals with Electron-Donating Ligands, Journal of the American Chemical Society, 136 ,2014 ,5161-5170.

Schattenmann, et al.,Opposition—Olefin Metatheses, ,Feb. 27, 2006.

U.S. Appl. No. 13/639,067, Notice of Allowance, dated Jan. 21, 2015, 19 pages.

13001297.4, Extended European Search Report, dated Nov. 6, 2013.

U.S. Appl. No. 14/001,811, Non-Final Office Action, dated Jun. 30, 2015, 14 pages.

U.S. Appl. No. 14/001,811, Notice of Allowance, dated Oct. 9, 2015, 5 pages.

Allen, et al., "Preparation of High Purity, Anionic Polymerization Grade Alkyl Methacrylate Monomers", Polymer Bulletin, 15, 1986, pp. 127-134.

Arndt, et al., "Synthesis and Reactions of Tungsten Alkylidene Complexes that Contain the 2,6-Dichlorophenylimido Ligand", Organometallics, 26, 2007, 1279-1290.

Bailey, et al., "Evaluation of Molybdenum and Tungsten Metathesis Catalysts for Homogeneous Tandem Alkane Metathesis", Organometallics, 28, 2009, pp. 355-360.

Bindl, et al., "Molybdenum Nitride Complexes with Ph3SiO Ligands are Exceedingly Practical and Tolerant Precatalysts for Alkyne

(56) References Cited

OTHER PUBLICATIONS

Metathesis and Efficient Nitrogen Transfer Agents", J Am Chem Soc., 1321(27), Jul. 15, 2009, 9468-9470.

Blanc, et al., "Dramatic Improvements of Well-Defined Silica Supported Mo-Based Olefin Metathesis Catalysts by Tuning the N-Containing Ligands", JACS, vol. 129 No. 27, 2007, pp. 8434-8435.

Blanc, et al., "Highly Active, Stable, and Selective Well-Defined Silica Supported Mo Imido Olefin Metathesis Catalysts", J. Am. Chem. Soc., 129, 2007, pp. 1044-1045.

Dolman, et al., "Enantioselective Synthesis of Cyclic Secondary Amines through Mo-Catalyzed Asymmetric Ring-Closing Metathesis (ARCM)", Organic Letters col. 5, No. 25, 2003, pp. 4899-4902.

EP13003540.5, Extended European Search Report, dated Dec. 11, 2013.

EP13003541.3, European Search Report, dated Nov. 25, 2013.

Flook, et al., "Z-Selective and Syndioselective Ring-Opening Metathesis Polymerization (ROMP) Initiated by Monoaryloxidepyrrolide (MAP) Catalysts", Macromolecules vol. 43 No. 18, 2010, pp. 7515-7522.

Fox, et al., "Synthesis of Five-and Six-Coordinate Alkylidene Complexes of the Type Mo (CHR) (NAr) [OCMe (CF3) 2Sx and Their Use as Living Romp Initiators or Wittig Reagents", American Chemical Society, Organometallics, 12, 1993, pp. 759-768.

Heppekausen, et al., "Practical New Silyloxy-Based Alkyne Metathesis Catalysts with Optimized Activity and Selectivity Profiles", J Am Chem Soc., vol. 132 No. 32, 2010, pp. 11045-11057.

Heppekausen, et al., "Rendering Schrock-type Molybdenum Alkylidene Complexes Air Stable: User-Friendly Precatalysts for Alkene Metathesis", Angewandte Chemie (International Ed.) vol. 123, No. 34, Aug. 16, 2011, pp. 7975-7978.

Jiang, et al., "Fundamental Studies of Tungsten Alkylidene Imido Monoalkoxidepyrrolide Complexes", J. Am. Chem. Soc. vol. 131, 2009, pp. 7770-7780.

Jiang, et al., "Highly Z-Selective Metathesis Homocoupling of Terminal Olefins", J. Am. Chem. Soc. 131, 2009, pp. 16630-16631.

Lee, et al., "Endo-Selective Enyne Ring-Closing Metathesis Promoted by Stereogenic-at-Mo Monoalkoxide and Monoaryloxide Complexes. Efficient Synthesis of Cyclic Dienes Not Accessible Through Reactions with Ru Carbines", J Am Chem Soc., 131(30), Aug. 5, 2009, 10652-10661.

Malcolmson, et al., "Highly efficient molybdenum-based catalysts for enantioselective alkene metathesis", Nature, vol. 456, Dec. 25, 2008, pp. 933-937.

Marinescu, et al., "Ethenolysis Reactions Catalyzed by Imido Alkylinene Monoaryloxide Monopyrrolide (MAP) Complexes of Molybdenum", Journal of the American Chemical Society, ACS Publications, US, vol. 131 No. 31, Aug. 12, 2009, 10840-10841.

Marinescu, et al., "Simple Molybdenum (IV) Olefin Complexes of the Type Mo(NR)(X)(Y)(olefin)", Organometallics, 29, 2010, pp. 6816-6828.

Marinescu, et al., "Syntheses of Variations of Stereogenic-at-Metal Imido Alkylidene Complexes of Molybdenum", Organometallics, vol. 31 No. 17, 2012, pp. 6336-6343.

Oskam, et al., "Rational Isomers of Mo(VI) Alkylidene Complexes and Cis/Trans Polymer Structure: Investigations in Ring-Opening Metathesis Polymerization", J. Am. Chem. Soc. 115, 1993, pp. 11831-11845.

PCT/DE2011/000348, International Search Report and Written Opinion with English Translation, dated Jul. 22, 2011, 10 pages.

PCT/DE2011/000348, International Preliminary Report on Patentability, dated Oct. 9, 2012, 5 pages.

PCT/DE2012/100047, International Search Report and Written Opinion (with English translation), dated Jul. 24, 2012, 10 pages.

PCT/DE2012/100047, International Preliminary Report on Patentability, dated Sep. 3, 2013, 6 pages.

PCT/EP2014/000671, International Search Report and Written Opinion, dated Dec. 16, 2014.

PCT/EP2014/001909, International Search Report and Written Opinion, dated Aug. 7, 2014.

PCT/EP2014/001910, International Search Report and Written Opinion, dated Sep. 24, 2014.

Rendon, et al., "Well-Defined Silica-Supported No-Alkylidene Catalyst Precursors Containing One or Subsitituent: Methods of Preparation and Structure-Reactivity Relationship in Alkene Metathesis", Chem. Euro. J., 15, 2009, pp. 5083-5089.

Schrock, et al., "Further Studies of Imido Alkylidene Complexes of Tungsten, Well-Characterized Olefin Metathesis Catalysts with Controllable Activity", Organometallics, 9(8), 1990, 2262-2275.

Schrock, "High Oxidation State Multiple Metal-Carbon Bonds", Chem Rev., 102, 2002, 145-179.

Schrock, "Multiple Metal-Carbon Bonds for Catalytic Metathesis Reactions (Nobel Lecture)", Angew Chem Int Ed Engl, 45(23), 2006, 3748-3759.

Schrock, "Recent Advances in High Oxidation State Mo and W Imido Alkylidene Chemistry", Chemical Reviews, vol. 109 No. 8, Mar. 13, 2009, pp. 3211-3226.

Schrock, et al., "Recent Advances in the Syntheses and Applications of Molybdenum and Tungsten Alkylidene and Alkylidene Catalysts for the Metathesis of Alkenes and Alkynes", Adv Sys Catal., 349, 2007, 55 pages.

Singh, et al., "Synthesis of Monoalkoxide Monopyrrolyl Complexes Mo(NR)(CHR')(OR")(pyrrolyl) Enyne Metathesis with High Oxidation State Catalysts", J. Am. Chem. Soc. 129, 2007, pp. 12654-12655.

Totland, et al., "Ring Opening Metathesis Polymerization with Binaphtholate or Biphenolate Complexes of Molybdenum", American Chemical Society, Macromolecules, 29, 1996, pp. 6114-6125.

Tsai, et al., "Facile Synthesis of Trialkoxymolybdenum(VI) Alkylidyne Complexes for Alkyne Metathesis", Organometallics, 19, 2000, 5260-5262.

Yu, et al., "Enol Ethers as Substrates for Effecient Z- and Enantioselective Ring-Opening/Cross-Metathesis Reactions Promoted by Sterogenis-at-Mo Complexes: Utility in Chemical Synthesis and Mechanistice Atrributes", J. Chem. Soc., 134, 2012, 2788-2799.

Yu, et al., "Synthesis of Macrocyclic Natural Products by Catalyst-Controlled Stereoselective Ring-Closing Metathesis", Nature, vol. 479 No. 7371, Nov. 2, 2011, pp. 89-93.

Yuan, "Pentafluorophenylimido Alkylidene Complexes of Molybdenum and Tungsten", Organometallics, vol. 31, 2012, pp. 4650-4653.

Meek, et al.,Catalytic Z-Selective Olefin Cross-Metathesis for Natural Product Synthesis, Nature 471 ,2011 ,461-466.

Notice of Allowance dated Jun. 1, 2018 for U.S. Appl. No. 14/903,119.

Office Action dated Feb. 14, 2018 for U.S. Appl. No. 14/209,313.

Office Action dated Aug. 10, 2018 for U.S. Appl. No. 14/209,313.

Office Action dated Dec. 11, 2018 for U.S. Appl. No. 14/904,172.

Office Action dated Dec. 17, 2018 for U.S. Appl. No. 15/536,446.

Duquette, et al.,ECSA Studies on Silica- and Alumina-Supported Rhenium Oxide Catalysts, J Catal. 90 ,1984 ,362.

Mougel, et al.,Low Temperature Activation of Supported Metathesis Catalysts by Organosilicon Reducing Agents, ACS Central Science, 2 ,2016 ,569-576.

Notice of Allowance dated Feb. 25, 2019 for U.S. Appl. No. 14/209,313.

Dreisch, et al.,Synthesis and Structure of Dimethoxyethane-Dichlorodioxo-Tungsten(VI)—a Highly Soluble Derivative of Tungsten Dioxidichloride, Polyhedron, 10(20-21) ,1991 ,2417-2421.

Gibson, et al.,The Use of Silyletheres and Silythioethers in Syntheses fo Oxohalide and Thiohalide Compounds of Molybdenum and Tungsten, Polyhedron, vol. 9 No. 18 ,1990 ,2293-2298.

Jeong, et al.,Syntheses of Tungsten tert-Butylimido and Adamantylimido Alkylidence Complexes Employing Pyridinium Chloride as the Acid, Organometallics, 31 ,2012 ,6522-6525.

Laguerre, et al.,Silylation Reductrice De Derives Monoaromatiques Fonctionnels, Journal of Organometallic Chemistry, 93 ,1975 ,C17-C19.

Ross-Medgaarden, et al.,Structural Detemination of Bulk and Surface Tungsten Oxides with UV-vis Diffuse Reflectance Spectroscopy and Raman Spectroscopy, J. Phys. Chem., 111 ,2007 ,15089-15099.

Schattenmann, et al.,Dissertation, Anorganisches Institut der Technischen Universitat Munchen, ,1997.

(56) References Cited

OTHER PUBLICATIONS

Patel, et al.,High Conversion and Productive Catalyst Turnovers in Cross-Metathesis Reactions of Natural Oils with 2-Butene, Green Chem., 8 ,2006 ,450-454.

* cited by examiner

IMMOBILIZED METATHESIS TUNGSTEN OXO ALKYLIDENE CATALYSTS AND USE THEREOF IN OLEFIN METATHESIS

DESCRIPTION

The invention relates to immobilized organometallic tungsten catalysts. The catalysts are useful in the heterogeneous catalysis of olefin metathesis.

Figure 1:
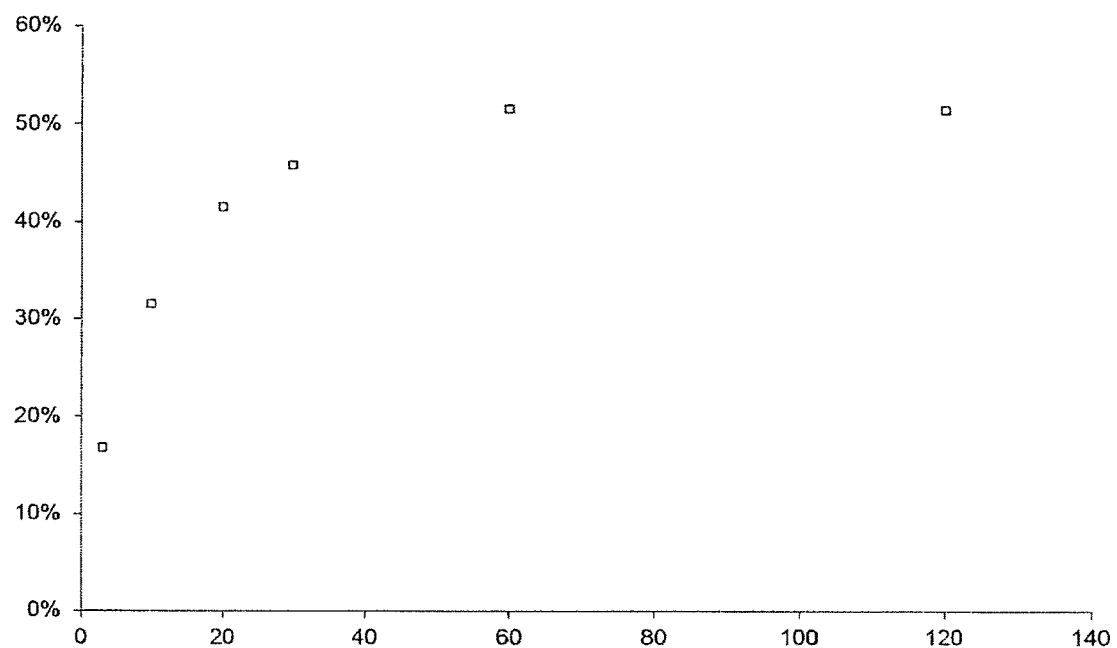
FIG. 1 is a plot of conversion versus time for cis-4-nonene metathesis.

Due to the growing importance of olefin metathesis, a great need exists for providing suitable catalysts which beneficially perform at industrial scale. A considerable number of organometallic tungsten catalysts is already known to homogeneously catalyze olefin metathesis. Although it is further known that in general heterogeneous catalysts may be easier separated off from reaction mixtures than homogeneous catalysts, e.g. by filtration, which is an advantage particular at industrial scale, comparatively few heterogeneous tungsten catalysts have been accessible for olefin metathesis.

Rhers et al., Organometallics, 2006, vol. 25, 3554, disclose the formation of ethene and butenes, including 1-butene, from propene in a self-metathesis reaction by a silica supported tungsten catalyst. The catalyst has been characterized as syn-[(SiO)(W(=NAr)(=CHtBu)(CH$_2$tBu)] (Ar=2,6-iPrC$_6$H$_3$) of following formula:

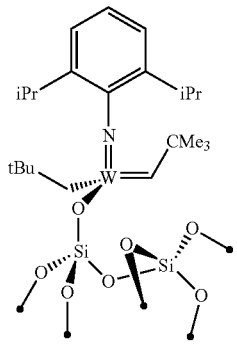

F. Blanc et al., Proc. Natl. Acad. Sci. USA, Aug. 26, 2008, vol. 105, no 34, 12123-12127, later disclose the selective formation of ethene and 2-butene from propene in a self-metathesis reaction by a silica supported tungsten catalyst. This reaction is a heterogeneously catalyzed. The catalyst is of the following structure:

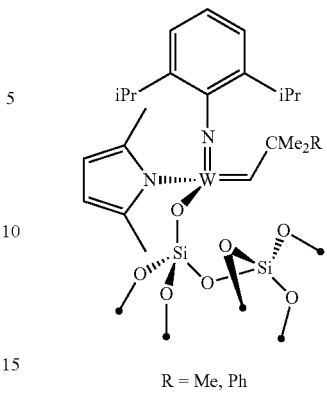

R = Me, Ph and is prepared by grafting [W(=N(2,6-diisopropylphenyl)(=CHtBu)(2,5-Me$_2$C$_4$H$_2$)$_2$] on SiO$_{2\text{-}(700)}$.

WO$_3$ on SiO$_2$ may also be used for metathesis reactions, however, such catalysts typically operate at rather elevated temperatures. E.g., http://handle.net/10413/896 describes the performance of a WO$_3$/SiO$_2$ catalyst for the metathesis of 1-hexene in an isothermal, gas-phase fixed bed tubular reactor between 420 and 500° C.

Mazoyer, E. et al. report the synthesis of an alkyl oxo tungsten derivative supported on silica as olefin metathesis catalyst (Chem. Commun. 2010, 46, 8944-8946). Herein, (tBuCH$_2$)$_3$XWO (X=alkyl, halogen, alkoxide, . . . ) was reported to react with silica, pretreated at 700° C., to give (≡SiO)(tBuCH$_2$)$_2$Cl(W=O) and/or (≡SiO)(tBuCH$_2$)$_3$(W=O), although a targeted alkylidene structure was (≡SiO)(tBuCH$_2$)X(W=O)(=CHt-Bu) (X=Cl or CH$_2$tBu). However, said supported catalyst works at relatively high temperature, >100° C., and the actual nature of the active site is unknown.

In view of the few known heterogeneous tungsten catalysts suitable for olefin metathesis, and in view of the limited suitability or applicability of such catalysts with respect to the variety of metathesis reactions and olefins employed in metathesis reactions, a great need still remains for providing further heterogeneous catalysts based on tungsten which in particular perform at industrial scale and which may be employed at low temperatures.

Thus, one object of the present invention is the provision of immobilized tungsten catalysts which may be used for the heterogeneous catalysis of olefin metathesis, whose efficacy may be purposively adapted to the various types of olefin metathesis, and which perform at industrial scale, preferably at low temperatures.

The inventors of the present invention have surprisingly discovered that by reaction of tungsten oxo alkylidene complexes with silica (SiO$_2$) or a support comprising silica, and depending on the heat pretreatment of silica, tungsten oxy moieties may be bonded to silica forming structures which may be characterized as (A): (≡SiO)$_2$W(=O)(=CR$^1$R$^2$)

or by a (≡SiO)W(=O)(=CR$^1$R$^2$) moiety which in turn bears (B) a residue R$^3$ or R$^4$ stemming from the tungsten oxo alkylidene complexes employed as starting material such forming a structure (≡SiO)W(=O)(=CR$^1$R$^2$)(R$^3$) or (≡SiO)W(=O)(=CR$^1$R$^2$)(R$^4$); or (C) said residue R$^3$, and wherein additionally structures are present bearing said residue R$^4$ such forming structures (≡SiO)W(=O)(=CR$^1$R$^2$)(R$^3$) and (≡SiO)W(=O)(=CR$^1$R$^2$)(R$^4$).

It is possible that as by-product minor amounts of structures are generated which may be characterized by
(D) (≡SiO)W(=O)(—CHR$^1$R$^2$)(R$^3$)(R$^4$).

Said structures (A), (B) and (C) stemming from said residues R$^3$ or R$^4$ and/or said residues R$^1$ and R$^2$ attached to W may be selected such that the efficacy of the immobilized tungsten oxo alkylidene catalysts according to the invention may be adapted to a particular olefin metathesis.

Thus, the compounds according to the invention comprising or consisting of (≡SiO)$_x$W(=O)(=CR$^1$R$^2$)(R$^3$ or R$^4$)$_{2-x}$ with x=1 or 2 may be prepared by grafting appropriate precursor compounds on silica or on a support comprising silica.

First Aspect of the Invention: Preparation of the Catalyst According to the Invention According to a first aspect, the invention relates to a method of making a tungsten catalyst comprising or consisting of (≡SiO)$_x$W(=O)(=CR$^1$R$^2$)(R$^3$ or R$^4$)$_{2-x}$, wherein each of R$^1$ and R$^2$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;

each R is independently hydrogen or an optionally substituted group selected from C$_{1-20}$ aliphatic, C$_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

R$^3$ and R$^4$ have independently the same meaning as R$^1$ and R$^2$; or tris(C$_{1-20}$ alkyl)silyl, tris(C$_{1-20}$ alkyl)silyloxy, tris (C$_{1-20}$ alkoxy)silyl, tris(C$_{1-20}$ alkoxy)silyloxy, tris(aryl)silyl, tris(aryl)silyloxy, tris(aryloxy)silyl, or tris(aryloxy)silyloxy; and
wherein x=1 or 2,
comprising at least the following step (i):
(i) reacting silica with a tungsten oxo alkylidene complex comprising or consisting of (R$^3$)(R$^4$)W(=O)(=CR$^1$R$^2$)(L)$_y$, wherein y=0, 1, or 2, and L is a neutral ligand, wherein R$^1$, R$^2$, R$^3$ and R$^4$ have the meaning as defined above, and wherein R$^3$ and R$^4$ additionally may have the meaning of halogen, preferably of Cl.

Neutral ligands L are compounds having a pair of electrons such that said compound is an electron donor. Preferred neutral ligands are selected from phosphine, dialkyl ether, amine or nitrile.

In one embodiment, said tungsten catalyst comprising (≡SiO)$_x$W(=O)(=CR$^1$R$^2$)(R$^3$ or R$^4$)$_{2-x}$ may further comprise said ligand L or non-stoichiometric amounts of L. Accordingly, in one embodiment, the invention relates to a method of making a tungsten catalyst comprising or consisting of (≡SiO)$_x$W(=O)(=CR$^1$R$^2$)(R$^3$ or R$^4$)$_{2-x}$(L)$_z$ wherein z=0, 1 or 2, or any number between 0 and 2.

Accordingly, the term "(≡SiO)$_x$W(=O)(=CR$^1$R$^2$)(R$^3$ or R$^4$)$_{2-x}$" is interchangeably used with the term "(≡SiO)$_x$W (=O)(=CR$^1$R$^2$)(R$^3$ or R$^4$)$_{2-x}$(L)$_z$".

Contrary to homogeneous catalysis, where the catalyst frequently has to be separated off by a rather complex processing of the reaction mixture, whereby the catalyst often is destroyed or at least considerably deteriorated in its activity, the catalysts according to the invention may be separated off from the reaction mixture via simple processing, e.g. by filtration or centrifugation. Furthermore, the catalysts may be employed at rather low temperature, e.g. at 15 to 50° C. The catalysts may be re-used in olefin metathesis. This is particularly beneficial at an industrial scale.

In a preferred embodiment of the tungsten catalyst, R$^1$ and R$^2$ can be the same or different and are hydrogen, C$_{1-20}$ alkyl, C$_{1-20}$ alkenyl, C$_{1-20}$ heteroalkyl, C$_{1-20}$ heteroalkenyl, aryl, or heteroaryl, optionally substituted, respectively; and each of R$^3$ and R$^4$ is an anionic ligand, and is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;

each R is independently hydrogen or an optionally substituted group selected from C$_{1-20}$ aliphatic, C$_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

R$^3$ and R$^4$ have independently the same meaning as R$^1$ and R$^2$; or tris(C$_{1-20}$ alkyl)silyl, tris(C$_{1-20}$ alkyl)silyloxy, tris (C$_{1-20}$ alkoxy)silyl, tris(C$_{1-20}$ alkoxy)silyloxy, tris(aryl)silyl, tris(aryl)silyloxy, tris(aryloxy)silyl, or tris(aryloxy)silyloxy.

In a further preferred embodiment of the catalyst, R$^1$ and R$^2$ can be the same or different and are hydrogen, C$_{1-20}$ alkyl, C$_{1-20}$ alkenyl, C$_{1-20}$ heteroalkyl, C$_{1-20}$ heteroalkenyl, aryl, or heteroaryl, optionally substituted, respectively; and each of $R^3$ and $R^4$ is independently R, —OR, $N(R)_2$, further preferably —OR or $N(R)_2$.

In one embodiment, tungsten oxo alkylidene complexes useful in the method according to the invention are of general formula

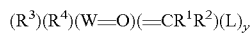

$(R^3)(R^4)(W=O)(=CR^1R^2)(L)_y$ wherein
each of $R^1$ and $R^2$ has the meaning as defined above, and each of $R^3$ and $R^4$ has the meaning as defined above, preferably the meaning of R or —OR or —$N(R)_2$ or halogen, and wherein L and y have the meaning as defined above.

In one embodiment, the tungsten oxo alkylidene complex is of general formula

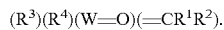

$(R^3)(R^4)(W=O)(=CR^1R^2)$.

Tungsten oxo alkylidene complexes useful in the method of the invention are known or may be prepared according to known methods, e.g. according to US 2013/0116434 A1 or D. V. Perishkov, R. R. Schrock, Organometallics (2012), 31, 7278.

The following terms in quotation marks are used in the meaning of the invention.

The term "$C_{1-20}$ aliphatic" encompasses both alkyl and alkenyl.

The term "alkyl" encompasses saturated aliphatic groups, including straight-chain alkyl groups, branched-chain alkyl groups, cycloalkyl (alicyclic) groups, alkyl substituted cycloalkyl groups, and cycloalkyl substituted alkyl groups and alkyl groups substituted with aryl. In certain embodiments, a straight chain or branched chain alkyl has about 20 or fewer carbon atoms in its backbone (e.g., $C_{1-20}$ for straight chain, $C_{3-20}$ for branched chain). Likewise, cycloalkyls have from about 3 to about 10 carbon atoms in their ring structure, and alternatively about 5, 6 or 7 carbons in the ring structure. In some embodiments, an alkyl group may be a lower alkyl group, wherein a lower alkyl group comprises 10 or fewer carbon atoms in its backbone (e.g., $C_{1-10}$ for straight chain lower alkyls).

In one embodiment, the term "alkyl" encompasses $C_{1-4}$ alkyl such as methyl, isopropyl iPr) or t-butyl ("tBu"). The term "$tBu_{F3}$" denotes a tertiary butyl group $(CF_3)(CH_3)_2C$. The term "$tBu_{F6}$" denotes a tertiary butyl group $(CF_3)_2(CH_3)C$. The term "$tBu_{F9}$" denotes a tertiary butyl group $(CF_3)_3C$.

The term "alkyl" also encompasses bridged hydrocarbon residues such as the adamantyl residue, particularly the adamant-1-yl residue.

The term "alkyl" also encompasses annelated ring systems such as the fluorene-9-yl residue such as the 9-phenyl-fluorene-9-yl residue.

The term "alkenyl" refers to olefinic groups as described below. The alkenyl group may be optionally substituted with the substituents defined above.

The term "$C_{1-20}$ heteroalkyl" refers to alkyl groups in which one or more atoms is a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "alkoxy" refers to the group —O-alkyl, wherein alkyl has the meaning as defined above in connection with the term alkyl.

The term "aryl ring" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl).

That is, at least one ring may have a conjugated π electron system, while other, adjoining rings can be cycloalkyls, cycloalkenyls, cycloalkynyls, aryls, and/or heterocyclyls. The aryl group may be optionally substituted.

The term "aryloxy" refers to the group —O-aryl, wherein aryl has the meaning as defined above in connection with the term alkyl.

The term "carbocyclic aryl groups" refers to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the aryl groups may include monocyclic carbocyclic aryl groups and polycyclic or fused compounds (e.g., two or more adjacent ring atoms are common to two adjoining rings) such as naphthyl group. Non-limiting examples of aryl groups include phenyl, naphthyl, tetrahydronaphthyl, indanyl, indenyl, and the like.

The term "heteroaryl" refers to aryl groups in which one or more atoms is a heteroatom (e.g., oxygen, nitrogen, sulfur, and the like), optionally substituted. Examples of aryl and heteroaryl groups include, but are not limited to, phenyl, pyrrolyl, furanyl, imidazolyl, oxazolyl, thiazolyl, triazolyl, pyrazolyl, pyridinyl, pyrazinyl, pyridazinyl and pyrimidinyl, and the like.

A preferred heteroaryl residue is the pyrrol-1-yl residue (py) or 2,5-dimethylpyrrol-1-yl (2,5-$Me_2$py or $Me_2$pyr) or 2,5-diphenylpyrrol-1-yl (2,5-$Ph_2$pyr). The pyrrol-1-moiety is also termed as pyrrolide.

The terms "substituted" and "optionally substituted" are contemplated to include all permissible substituents of organic compounds, "Permissible" being in the context of the chemical rules of valence known to those of ordinary skill in the art. Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl.

The term "comprising" is used in the meaning of "including but not limited to".

The term "consisting of" is used in the meaning "including and limited to".

The catalyst according to the invention is heterogeneous, i.e. it comprises a solid support. Said solid support comprises "silica" or consists of "silica".

The term "solid support" encompasses any material that includes silica such as silica as such or silica in combination with other materials. Accordingly, silica may be used in the form of a mixed oxide, e.g. a mixed oxide of silica and alumina or silica and zirconia or oxides such as $TiO_2$, $V_2O_5$, $MoO_2$, $WO_3$, silicates, zeolites, or sulfates or phosphates of alkali metals or earth alkali metals. Preferably, silica is used as solid support.

The term "silica" encompasses compounds of formula $SiO_2$ and further encompasses porous or non-porous silica.

The term "silica" further encompasses partially dehydroxylated and/or dehydrated silica. Dehydroxylation and/or dehydration may be performed using elevated temperature or elevated temperature and vacuum. Residual hydroxyl content may be determined by titration with MeMgCl.

Hydroxyl content may be freely selected depending on drying temperature and drying time. Accordingly, the silica used for the compounds according to the invention may be adjusted in a tailor-made manner to the required properties of the W-compound to be immobilized. In this regard it is noteworthy that depending on the number of mmol of hydroxyl groups per gram silica, the amount of W compound per gram of silica and ultimately the activity of the resulting catalyst may be adjusted depending upon needs.

Preferably, prior to step (i), silica is heated in a temperature range of from 150 to 1,000° C., preferably employing vacuum or a flow of dry air or inert gas such as nitrogen or argon.

In a further preferred embodiment, silica is subjected to a temperature in the range of from 300 to 800° C. under pressure ranging from $10^{-6}$ mbar to 1 bar or a flow of dry air or inert gas such as nitrogen or argon, preferably for a period ranging from 4 to 24 h. Temperature and pressure may be performed in ramps.

Preferably, hydroxyl content determined by means of titration with MeMgCl ranges from 0.05 mmol to 2.00 mmol per g silica, further preferred from 0.1 mmol to 2 mmol per g silica.

In one embodiment, silica is partially dehydroxylated and dehydrated at 700° C. ($SiO_{2-(700)}$). However, other temperatures or temperature ranges may also be used depending on the requirements of the catalyst to be prepared and to be used as heterogeneous catalyst.

Thus, preferably, a silica is used in the method according to the invention which is partially dehydroxylated and dehydrated. Preferably, silica is dehydroxylated and dehydrated at elevated temperature, preferably at elevated temperature and in vacuo or a flow of dry air or inert gas such as nitrogen or argon.

If silica or silca comprised in a solid support is heated at relative low temperatures, the method according to the invention predominatly or exclusively results in a structure of formula $(\equiv SiO)_2W(=O)(=CR^1R^2)$ [according to structure (A)].

If silica or silca comprised in a solid support is heated at relative high temperatures, the method according to the invention predominantly or exclusively results in structures of formula $(\equiv SiO)W(=O)(=CR^1R^2)(R^3$ or $R^4)$ [according to structures (B) and/or (C)], wherein as by-product structure $(\equiv SiO)W(=O)(—CHR^1R^2)(R^3)(R^4)$ [according to structure (D)] may be formed.

The term "relative low temperatures" relates to a temperature range of from 150 to 300° C., preferably 180 to 250° C., more preferably 200° C.

The term "relative high temperatures" relates to a temperature range of 400 to 1,000° C., preferably 600 to 800° C., more preferably 700° C.

Thus, when selecting a medium temperature range, it is conceivable to generate a mixture of structures comprising or consisting both of $(\equiv SiO)_2W(=O)(=CR^1R^2)$ and $(\equiv SiO)W(=O)(=CR^1R^2)(R^3$ or $R^4)$, i.e. structures (A), (B), (C) and, optionally, (D).

The term "medium temperatures" preferably relates to a temperature range of from 200 to 600° C., more preferably 300 to 500° C.

Accordingly, in one embodiment, the method comprises at least step (0.1) or (0.2) or (0.3) prior to step (i):
(0.1) heating silica or heating silica in vacuo; or
(0.2) heating silica or heating silica in vacuo or heating silica in a flow of dry air or inert gas in a temperature range of from 150° C. to 300° C., wherein structure of formula $(\equiv SiO)_2W(=O)(=CR^1R^2)$ is obtained; or
(0.3) heating silica or heating silica in vacuo or heating silica in a flow of dry air or inert gas in a temperature range of from 600° C. to 800° C., wherein structures comprising or consisting of $(\equiv SiO)W(=O)(=CR^1R^2)(R^3$ or $R^4)$ are obtained.

Alternatively, the method comprises at least step (0.4):
(0.4) calcining silica at 500° C., rehydrating the calcined product at 200° C., and dehydroxylating the rehydrated product at 200° C. or higher.

In a preferred embodiment, $=CR^1R^2$ is selected from $=CHC(CH_3)_3$ or $=CH(C(CH_3)_2C_6H_5$.

In another preferred embodiment, $R^3$ and $R^4$ are independently $—N(R)_2$, preferably pyrrol-1-yl, 2,5-dimethylpyrrol-1-yl, or 2,5-diphenylpyrrol-1-yl, or —OR, wherein R is a six membered or 10 membered aryl ring, optionally substituted, or —OR is $C_{1-4}$ alkyl such as $(CF_3)(CH_3)_2CO$, $(CF_3)_2(CH_3)CO$, $(CF_3)_3CO$, $(C_6H_5)(CF_3)_2CO$ or $(CH_3)_3CO$.

In a further preferred embodiment, R in —OR is phenyl or annelated phenyl substituted with one or more of: $C_{1-4}$ alkyl, $C_{1-4}$ alkoxy, optionally substituted phenyl, optionally substituted phenoxy, halogen.

The term "halogen" refers to F, Cl, Br, I.

In a further preferred embodiment, $=CR^1R^2$ is selected from $=CHC(CH_3)_3$ or $=CH(C(CH_3)_2C_6H_5$ and $R^3=R^4=$—OR, wherein R is phenyl or annelated phenyl substituted with one or more of: $C_{1-4}$ alkyl, $C_{1-4}$ alkoxy, optionally substituted phenyl, optionally substituted phenoxy, halogen.

In a further preferred embodiment, $=CR^1R^2$ is selected from $=CHC(CH_3)_3$ or $=CHC(CH_3)_2C_6H_5$ and $R^3=$—OR, wherein R is phenyl or annelated phenyl substituted with one or more of: $C_{1-4}$ alkyl, $C_{1-4}$ alkoxy, optionally substituted phenyl, optionally substituted phenoxy, halogen; and $R^4=$—$N(R)_2$, preferably pyrrol-1-yl, 2,5-dimethylpyrrol-1-yl, or 2,5-diphenylpyrrol-1-yl.

Preferably, R in —OR is selected from 2,6-dimethylphenyl, 2,6-diisopropylphenyl, 2,6-ditertiobutylphenyl, 2,6-diadamantylphenyl, 2,6-dimesitylphenyl, 2,6-di(trifluoromethyl)phenyl, 2,6-dichlorophenyl, 2,6-diphenylphenyl, 2,6-diphenoxyphenyl, pentafluorophenyl, 2-(trifluoromethyl) phenyl, 2,3,5,6-tetraphenylphenyl Further preferred residues R in —OR are 4-fluoro-2,6-dimesitylphenyl or 2,6-di-tert.-butylphenyl, 4-bromo-2,6-di-tert.-butylphenyl or 4-methoxy-2,6-di-tert.-butylphenyl or 4-methyl-2,6-di-tert.-butylphenyl or 2,4,6-tri-tert.-butylphenyl or 2,3,5,6-tetraphenylphenyl or 4-bromo-2,3,5,6-tetraphenylphenyl or 2,6-di(4-bromophenyl)-3,5-diphenylphenyl or 4-bromo-2,6-di(4-bromophenyl)-3,5-diphenylphenyl.

In one embodiment, $=CR^1R^2$ is selected from $=CHC(CH_3)_3$ or $=CH(C(CH_3)_2C_6H_5$ and $R^3=R^4=$—$N(R)_2$, preferably pyrrol-1-yl, 2,5-dimethylpyrrol-1-yl, or 2,5-diphenylpyrrol-1-yl.

The catalysts according to the invention may be prepared by contacting a solution or suspension of the tungsten oxo alkylidene complex with a suspension of silica, preferably $SiO_{2-(700)}$, and stirring same at room temperature, e.g. for a period of from 2 to 24 h, preferably 6 to 18 h, whereby reaction (grafting) occurs. Aromatics such as toluene or benzene, chlorinated hydrocarbons such as dichloromethane or chlorobenzene, or hydrocarbons such as heptane or octane or ethers such as tetrahydrofuran may be used as solvents. The proceeding of the reaction (grafting) may be frequently observed by fading of the color of the solution or suspension and a coloration of silica. The catalyst may be separated off, e.g. by filtration, and may be dried, preferably applying temperature and vacuum.

Accordingly, step (i) may be further characterized in that the reaction is carried out in an organic solvent.

Moreover, the method according to the invention according to step (i) may be further characterized in that the temperature employed in step (i) is from −80 to 150° C., preferably 0 to 80° C.

The method may be further characterized in that same comprises besides step (i) at least one further step (ii) or step (ii) and step (iii):
(i) reacting silica or silica comprised in a solid support with a tungsten oxo alkylidene complex comprising or consisting of $(R^3)(R^4)W(=O)(=CR^1R^2)(L)_Y$ in an organic solvent;
(ii) isolating the product obtained in step (i), and
(iii) drying the product obtained in step (ii).

In another embodiment, the catalysts according to the invention are prepared by mixing the solid tungsten oxo alkylidene complex with solid silica.

In an alternative embodiment, the method may be further characterized in that same comprises step (i):
(i) reacting silica or silica comprised in a solid support with a tungsten oxo alkylidene complex comprising or consisting of $(R^3)(R^4)W(=O)(=CR^1R^2)(L)_Y$ in solid state.

Preferably, the catalysts are stored under an inert gas such as nitrogen or argon.

Second Aspect: Tungsten Oxo Alkylidene Catalysts According to the Invention

According to a second aspect, the invention relates to a tungsten catalyst comprising or consisting of $(\equiv SiO)_X W(=O)(=CR^1R^2)(R^3 \text{ or } R^4)_{2-x}$, wherein
each of $R^1$ and $R^2$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;
each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:
two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:
two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;
$R^3$ and $R^4$ have independently the same meaning as $R^1$ and $R^2$; or tris($C_{1-20}$ alkyl)silyl, tris($C_{1-20}$ alkyl)silyloxy, tris($C_{1-20}$ alkoxy)silyl, tris($C_{1-20}$ alkoxy)silyloxy, tris(aryl)silyl, tris(aryl)silyloxy, tris(aryloxy)silyl, or tris(aryloxy)silyloxy; and
wherein x=1 or 2.

In one embodiment, said tungsten catalyst comprising $(\equiv SiO)_X W(=O)(=CR^1R^2)(R^3 \text{ or } R^4)_{2-x}$ may further comprise a ligand L. Accordingly, in one embodiment, the invention relates to a tungsten catalyst comprising or consisting of $(\equiv SiO)_X W(=O)(=CR^1R^2)(R^3 \text{ or } R^4)_{2-x}(L)_z$ wherein z=0, 1 or 2, or any number between 0 and 2; and ligand L is a neutral ligand, preferably selected from phosphine, dialkyl ether, amine or nitrile. $R^1$, $R^2$, $R^3$ and $R^4$ have the meaning as defined above.

Said tungsten catalyst may be prepared according to a method as defined in the first aspect and any embodiment specified therein. Thus, the tungsten catalyst may have any structure as specified in the first aspect.

The compounds according to the invention may be used in the various known types of metathesis reaction.

Third Aspect: Use of the Catalysts According to the Invention

The compounds defined in the second aspect may be used for reacting compounds having an olefinic double bond in a metathesis reaction.

Thus, according to a third aspect, the invention relates to a method of forming an olefin from a first olefin and a second olefin in a metathesis reaction, comprising step (i):
(i) reacting the first olefin with the second olefin in the presence of a compound as defined in the second aspect or prepared according to the first aspect.

The term "reacting" encompasses a reaction in which in a compound a new bond is formed.

The term "olefinic double bond" refers to a carbon-carbon double bond or ethylenic double bond in a first olefin and a second olefin.

The term "first or second olefin" as used in this disclosure is in one embodiment synonymously used with the term "first and second olefin".

The term "olefin" as used in the terms "first olefin" and "second olefin" refers to any species having at least one ethylenic double bond such as linear and branched chain aliphatic olefins, cycloaliphatic olefins, or aryl substituted olefins. Olefins may comprise terminal double bond(s) ("terminal olefin") and/or internal double bond(s) ("internal olefin") and can be cyclic or acyclic, linear or branched, optionally substituted. The total number of carbon atoms can be from 2 to 100, or from 2 to 40; the double bonds of a terminal olefin may be mono- or bi-substituted and the double bond of an internal olefin may be bi-, tri-, or tetrasubstituted. In some cases, an internal olefin is bisubstituted.

Non-limiting examples of terminal olefins are substituted and unsubstituted linear alkyl internal olefins such as $C_4$-$C_{30}$ olefins (e.g., 1-butene, 1-pentene, 1-hexene, 1-heptene, 1-octene, 1-decene, 1-dodecene, 1-tetradecene, 1-hexadecene, 1-octadecene, 1-eicosene, allylbenzene, allyltrimethylsilane, methyl-10-undecenoate, allylboronic acid pincol ester, allylbenzylether, N-allyl-4-methylbenzenesulfonamide, allylaniline, methyl-9-decenoate, allyloxy(tert-butyl) dimethyl silane, allylcyclohexane, etc.).

In one embodiment, the olefin having a terminal olefinic double bond is of formula RCH=CH$_2$, wherein R is selected from H, alkyl, alkenyl, aryl, heteroalkyl, heteroalkenyl, heteroaryl, or acyl, optionally substituted.

The term "cyclic olefin" refers to any cyclic species comprising at least one ethylenic double bond in a ring. The atoms of the ring may be optionally substituted. The ring may comprise any number of carbon atoms and/or heteroatoms. In some cases, the cyclic olefin may comprise more than one ring. A ring may comprise at least 3, at least 4, at least 5, at least 6, at least 7, at least 8, or more, atoms. Non-limiting examples of cyclic olefins include norbornene, dicyclopentadiene, bicyclo compounds, oxabicyclo compounds, and the like, all optionally substituted. "Bicyclo compounds" are a class of compounds consisting of two rings only, having two or more atoms in common. "Oxabicyclo compounds" are a class of compounds consisting of two rings only, having two or more atoms in common, wherein at least one ring comprises an oxygen atom.

In another embodiment, the first and the second olefin or the first and the second olefin may bear one or more functional groups.

Preferably, the first and the second olefin or the first or the second olefin may bear one or more functional groups independently selected from the group consisting of ether, ester, amide, amine, halogen, nitrile, thioether, thioester, aryl, or heteroaryl.

In a further preferred embodiment, the first and the second olefin or the first or the second olefin bear one or more functional groups independently selected from alkoxy, aryloxy, perhaloalkoxy, arylalkoxy, heteroaryl, heteroaryloxy, heteroarylalkyl, heteroarylalkoxy, amino, halogen, alkylthio, oxo, carboxy esters, carboxamido, acyloxy, aminoalkyl, alkylaminoaryl, alkylaminoalkyl, alkoxyaryl, arylamino, arylalkylamino, alkylsulfonyl, carboxamidoalkylaryl, carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl.

The term "metathesis" refers to alkene (olefin) metathesis, and to the various types of metathesis such as cross metathesis, ring opening metathesis, ring opening polymerization metathesis, ring closing metathesis, ethenolysis, self or homo metathesis.

The term "cross metathesis" encompasses the reaction between two different olefins.

The term "ring opening metathesis" encompasses the ring opening of a cyclic alkene.

The term "ring opening polymerization metathesis" encompasses the ring opening of a cyclic alkene, wherein the ring-opened product polymerizes in a chain-growth polymerization to form a polymer containing olefinic bonds.

The term "ring closing metathesis" encompasses the ring closing of a diene.

The term "ethenolysis" encompasses the reaction of an olefin having an internal olefinic bond with ethylene.

The term "self or homo metathesis (SM)" encompasses the reaction between two identical olefins. The term is synonymously used with the term "homo cross metathesis (HCM)" and also encompasses the formation of an internal olefin from two identical olefins.

The structure of the first and the second olefin may be vastly freely selected.

Preferably,
(a) the first olefin and the second olefin are identical [homo or self-metathesis (SM)]; or
(b) the first and the second olefin are different from one another [cross metathesis (CM)]; or
(c) the first olefin has an internal olefinic double bond and the second olefin is ethylene [ethenolysis]; or
(d) the first olefin is a cyclic olefin and the second olefin is a cyclic olefin, wherein the first and the second olefin may be identical or may be different from one another [cross metathesis (SM) or (CM)]; or
(e) the first olefin is a diene and the second olefin is a diene, wherein the first olefin and the second olefin are identical, wherein step (i) results in the ring closing of the diene [ring closing metathesis (RCM)]; or
(f) the first olefin is a cyclic olefin and the second olefin is a cyclic olefin, wherein the first olefin and the second olefin are identical, wherein step (i) results in a ring opening metathesis polymerization (ROMP); or
(g) the first olefin is a cyclic olefin and the second olefin is a cyclic olefin, wherein the first olefin and the second olefin are identical, wherein step (i) results in a ring opening metathesis followed by a ring-closing metathesis reaction (ROM-RCM);
(h) the first olefin is a terminal diene and the second olefin is a terminal diene, wherein the first olefin and the second olefin are identical, and wherein step (i) results in a acyclic diene metathesis polymerization (ADMET), wherein a polyene and ethylene are generated.

Preferably, the method according to step (i) is carried out in a solvent, which dissolves the olefins and suspends the catalyst. Suitable solvents are solvents selected from aromatic solvents, preferably toluene, halogenated solvents, preferably chlorobenzene or methylene dichloride, alkanes, preferably pentane or hexane or octane. However, step (i) may be carried out without solvent, preferably if one of the olefins is a liquid under the reaction conditions. A reaction of the first and the second olefin in gaseous phase is likewise possible or the first olefin is in gaseous phase and the second olefin is in liquid phase.

The temperature employed in step (i) preferably ranges from −20° C. to 250° C., more preferably from 0° C. to 110° C., still more preferably from 15 to 50° C.

The concentration of the compound according to the invention used as catalyst in the method according to the invention can vary in broad ranges. Preferably, the catalyst is employed in a molar ratio of <5 mol % (calculated in terms of W), based on the first or the second olefin (100 mole %).

The proceeding of the reaction may be controlled preferably by gas or liquid chromatographic methods eventually coupled to Mass Spectrometry.

Preferably, the reaction is terminated by separating off the catalyst from the reaction mixture obtained in step (i). Separating off may be performed by methods such as filtration or centrifugation or distilling off the reaction mixture from the catalyst.

It has been surprisingly found that the compounds according to the invention after the separating off may be re-used in the reaction according to step (i) without considerable loss of activity and selectivity. This makes the compounds according to the invention particularly advantageous over respective homogeneous catalysts, which frequently require a complex processing of the reaction mixture obtained from metathesis, wherein the catalysts are often destroyed or at least considerably deteriorated in their activity.

Thus, the compounds according to the invention perform particularly beneficial at an industrial scale.

Accordingly, in one embodiment, the method according to the invention further comprises at least step (ii) or step (ii) and step (iii):
(ii) separating off the compound according to the invention from the reaction mixture obtained in step (i), preferably by filtration or centrifugation or distilling off the reaction mixture from the compound according to the invention;
(iii) re-using in step (i) the catalyst obtained in step (ii).

Thus, in general, the invention relates to the use of a compound as defined in the second aspect in a metathesis reaction.

Preferably, the metathesis reaction is selected from the group consisting of self-metathesis (SM), cross metathesis (CM), ring opening metathesis (ROM), ring closing metathesis (RCM), ROM-RCM, ring opening metathesis polymerization (ROMP), ethenolysis, and acyclic diene metathesis polymerization (ADMET).

EXAMPLES

General Considerations

All experiments were carried out under inert atmosphere using glovebox (Ar), Schlenk (Ar), or high vacuum ($10^{-5}$ mbar) techniques. [SiO$_{2-700}$] was prepared by calcining Aerosil-200 at 500° C. (5° C./min) under air for 4 h, exposed to high vacuum at the same temperature for 12 h, and heated to 700° C. (5° C./min) for 4 h under vacuum. Pentane, Et$_2$O, and toluene were dried by passage through two columns of activated alumina and degassed prior to use. Tetrahydrofuran (THF) was distilled from purple Na/benzophenone under Ar and stored over activated molecular sieves. Transmission infrared spectra were recorded on a Bruker Alpha FT-IR spectrometer. Elemental analyses were performed by the Mikroanalytisches Labor Pascher; Remagen, Germany.

Example 1

Preparation of a Catalyst 2 According to the Invention

SiO$_{2-(700)}$ (0.26 mmol SiOH g$^{-1}$) was reacted in step (i) with (ArO)$_2$W(=O)(=CHtBu) (1) (Ar=2,6-dimesitylphenyl; D. V. Perishkov, R. R. Schrock, Organometallics (2012), 31, 7278) to yield compound 2 according to the following reaction scheme:

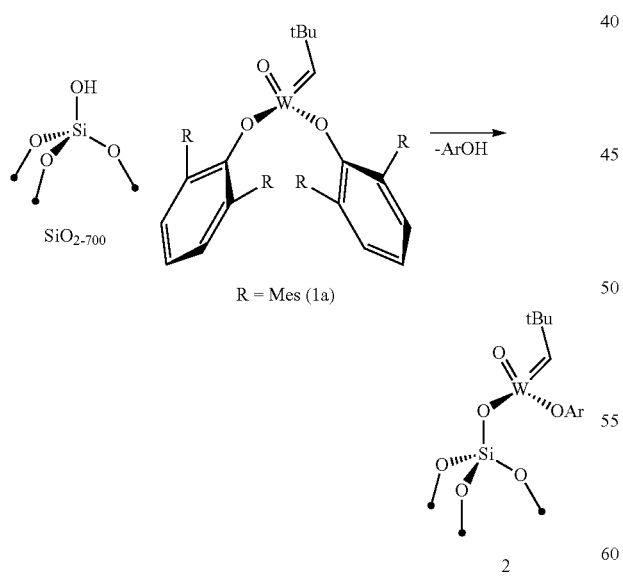

[SiO$_{2-700}$] (0.20 g, 0.052 mmol SiOH) was suspended in a yellow C$_6$H$_6$ (2 mL) solution containing (ArO)$_2$W(=O)(=CHtBu) (0.0504 g, 1.25 equiv) at 25° C. in an Ar filled glovebox. The slurry was maintained at this temperature for 3 h, then filtered and washed with C$_6$H$_6$ (3×2 mL) and pentane (1×10 mL) to yield the yellow material that was determined to contain [(≡SiO)W(=O)(=CHtBu)(OAr)]2 and small amounts of [(≡SiO)W(=O)(CH$_2$tBu)(OAr)$_2$] (20%) by solid state NMR spectroscopy and elemental analysis. The combined C$_6$H$_6$ washings contained 0.020 mmol of HOAr that was quantified by $^1$H NMR with Cp$_2$Fe internal standard. Elemental analysis: 4.38% C; 0.47% H; 1.71% W. $^1$H MAS NMR of [(≡SiO)W(=O)(=CHtBu)(OAr)] (2): 7.3 (W=CHtBu), 6.9, 2.2, 2.0, 1.0 ppm. $^{13}$C CP MAS NMR of [(≡SiO)W(=O)(=CHtBu)(OAr)] (2): 260 (W=CHtBu), 138, 131, 33, 21 ppm.

The reaction was monitored by infrared spectroscopy. The $v_{OH}$ associated with the silanols on the silica surface (3747 cm$^{-1}$) decreased upon contact with 1, though some free silanols persisted (40%). From quantitative mass balance analysis of recovered ArOH it can be estimated that ca. 60% of the silanols present in silica reacted with 1 to form [(≡SiO)W(=O)(=CHtBu)OAr]. In addition to the free silanol vibration the infrared spectrum of 2 contained a $v_{OH}$ at 3586 cm$^{-1}$ associated with surface silanols interacting with nearby aromatic residues, and $v_{CH}$ and $v_{CH}$ bands from the organic residues in 2. These results indicated that 1 grafted on [SiO$_{2-700}$] to form [(≡SiO)W(=O)(=CHtBu)(OAr)]. The elemental analysis of 2 gave 1.71% by weight W that suggests monomeric tungsten species on the silica surface, and 4.38% by weight C per tungsten, close to the expected value in 2.

In the solid-state $^1$H NMR, the alkylidene proton signal from [(≡SiO)W(=O)(=CHCMe$_3$)(OAr)] was observed as a shoulder at 7.6 ppm close to the aromatic signals.

Example 2

Preparation of a Catalyst 4 According to the Invention

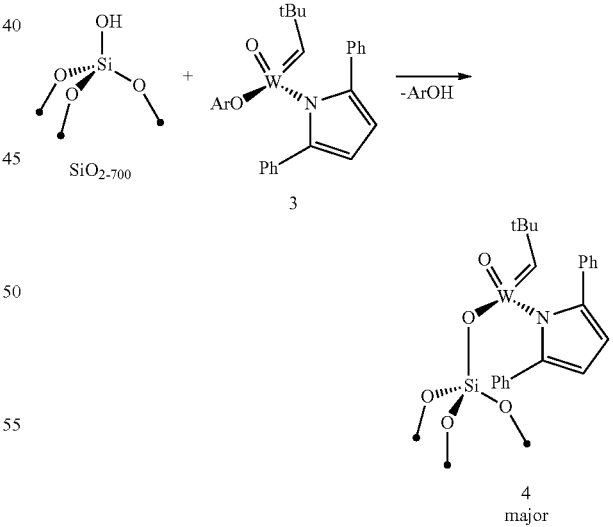

[SiO$_{2-700}$] (0.20 g, 0.052 mmol SiOH) was suspended in a yellow C$_6$H$_6$ (2 mL) solution containing (ArO)(2,5-Ph$_2$Pyr)W(=O)(=CHtBu) (3) (0.051 g, 1.25 equiv) at 25° C. in an Ar filled glovebox. The slurry was maintained at this temperature for 3 h, then filtered and washed with C$_6$H$_6$ (3×2 mL) and pentane (1×10 mL) to yield the yellow material that was determined to contain [(SiO)W(=O)(=CHtBu)(2,5-

Ph$_2$Pyr)] (4) along with small amounts (5-15%) of [(SiO)W(=O)(=CHtBu)(OAr)] (2) and [(SiO)W(=O)(CH$_2$tBu)(2,5-Ph$_2$Pyr)(OAr)] by solid state NMR spectroscopy and elemental analysis. The combined C$_6$H$_6$ washings contained 0.020 mmol of HOAr that was quantified by $^1$H NMR with Cp$_2$Fe internal standard. Elemental analysis: 4.38% C; 0.47% H; 1.71% W. $^1$H MAS NMR of [(SiO)W(=O)(=CHtBu)(2,5-Ph$_2$py)] (4): 9.8 (W=CHtBu), 7.5, 4.5, 2.3, 1.0 ppm.

Example 3

Preparation of a Catalyst 6 According to the Invention

SiO$_{2-(700)}$ (0.26 mmol SiOH g$^{-1}$) was reacted in step (i) with (dAdPO)$_2$W(=O)(=CHtBu) (5) (dAdPO=2,6-diadamantyl-4-methylphenoxide; D. V. Perishkov, W. P. Forrest, R. R. Schrock, S. J. Smith, P. Müller, Organometallics (2013), 32, 5256) to yield compound 6 according to the following reaction scheme:

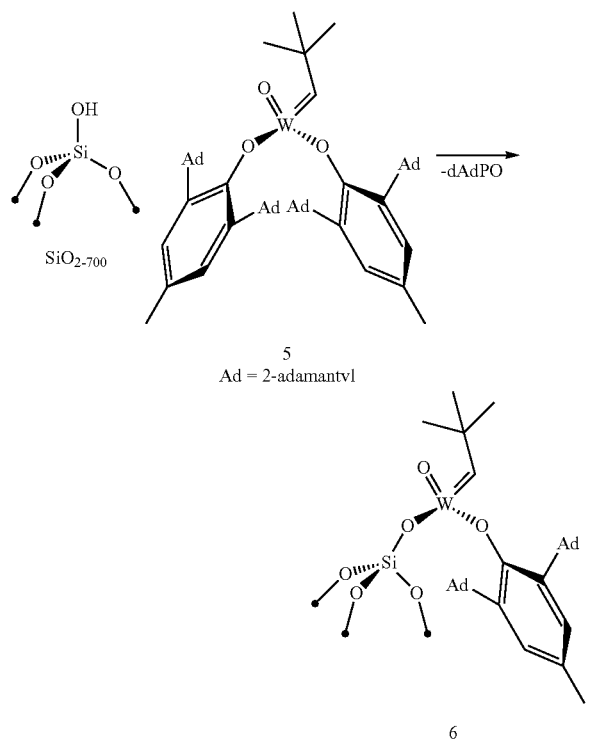

5
Ad = 2-adamantyl

6

[SiO$_{2-700}$] (0.60 g, 0.156 mmol SiOH) was suspended in a yellow C$_6$H$_6$ (2 mL) solution containing (dAdPO)$_2$W(=O)(=CHtBu) (0.193 g, 1.25 equiv) at 25° C. in an Ar filled glovebox. The slurry was maintained at this temperature for 3 h, then filtered and washed with C$_6$H$_6$ (3×2 mL) and pentane (1×10 mL) to yield the yellow material that was determined to contain [(SiO)W(=O)(=CHtBu)(dAdPO)]6 and small amounts of [(SiO)W(=O)(CH$_2$tBu)(dAdPO)$_2$] (<5%) by solid state NMR and elemental analysis. The combined C$_6$H$_6$ washings contained 0.037 mmol of dAdPOH that was quantified by $^1$H NMR with Cp$_2$Fe internal standard. Elemental analysis: 3.45% C; 1.37% W. $^1$H MAS NMR of [(SiO)W(=O)(=CHtBu)(dAdPO)] (6): 8.5 (W=CHtBu), 6.9, 1.9 ppm. $^{13}$C CP MAS NMR of [(SiO)W(=O)(=CHtBu)(dAdPO)] (6): 260 (W=CHtBu), 135, 128, 38, 32, 25, 15 ppm.

The reaction was monitored by infrared spectroscopy. The $v_{OH}$ associated with the silanols on the silica surface (3747 cm$^{-1}$) decreased upon contact with 5, though some amount of free silanols persisted (73%). From quantitative mass balance analysis of recovered ArOH it can be estimated that ca. 27% of the silanols present in silica reacted with 5 to form [(≡SiO)W(=O)(=CHtBu)(dAdPO)]. In addition to the free silanol vibration the infrared spectrum of 6 contained a $v_{OH}$ at 3624 cm$^{-1}$ associated with surface silanols interacting with nearby aromatic ligand residues, and $v_{CH}$ and $v_{CH}$ bands from the organic residues in 6. These results indicated that 5 grafted on [SiO$_{2-700}$] to form [(≡SiO)W(=O)(=CHtBu)(dAdPO)]. The elemental analysis of 6 gave 1.37% by weight W that suggests monomeric tungsten species on the silica surface, and 3.45% by weight C per tungsten, close to the expected value in 6.

In the solid-state $^1$H NMR, the alkylidene proton signal from [(≡SiO)W(=O)(=CHCMe$_3$)(OAr)] was observed as a shoulder at 7.6 ppm close to the aromatic signals.

Example 4

Metathesis

Catalytic Activity Measurements. Representative Procedure.

In an Ar filled glovebox scintillation vials were charged with compound 2. A solution of 0.8 M solution of alkene was added and the vial was maintained at 30° C. Aliquots of the reaction mixture were taken at various points and treated with EtOAc under air and subjected to gas chromatography analysis to determine the conversion and E/Z selectivity.

Figure 2:
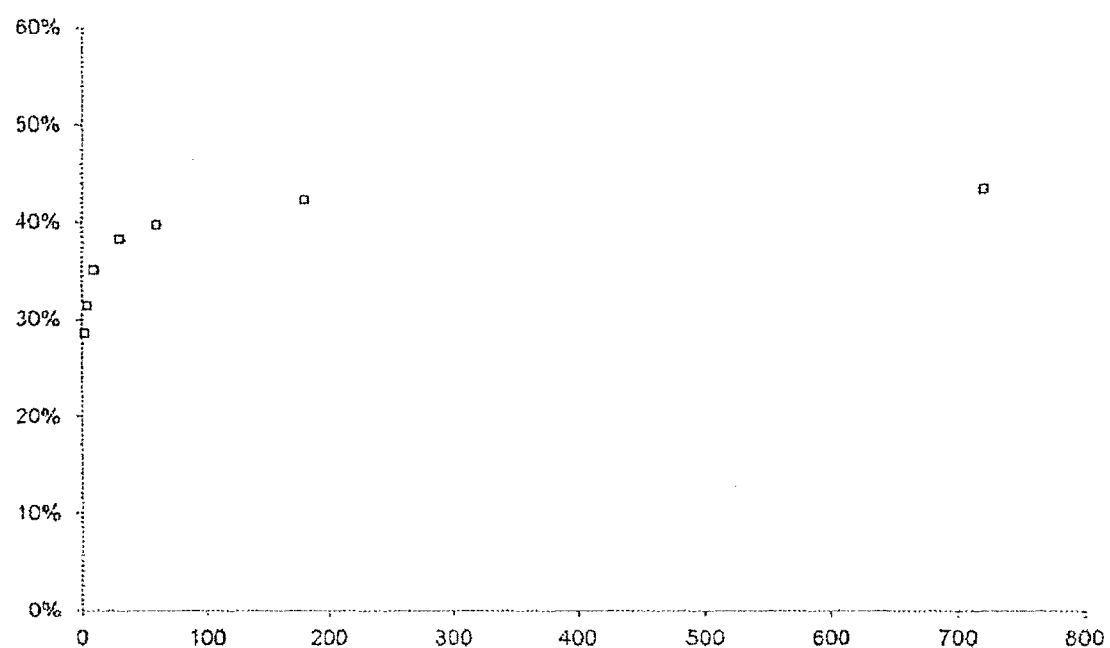
FIG. 2 is a plot of conversion versus time for ethyl oleate metathesis.

The catalytic activity of compound 2 in the self-metathesis of cis-4-nonene, 1-nonene and ethyl oleate was investigated. [(≡SiO)W(=O)(=CHtBu)(OAr)] has very high activity in olefin metathesis of olefins at 30° C. for all three substrates. A plot of conversion versus time for cis-4-nonene metathesis is shown in FIG. 1 (Y-axis: conversion %; x-axis: time [min]). On all three substrate described below, catalyst compound 2 is active in metathesis, resulting in the formation of homo metathesis products as the only products observable by GC (Table 1). The activity of ethyl oleate is particularly noteworthy {FIG. 2; metathesis of ethyl oleate (0.02 mol %, 30° C.) (Y-axis: conversion [%]; x-axis: time [min]}, since the WO$_3$/SiO$_2$ catalyst is not active in the presence of functionalized olefins. Similarly, compound 4 displays very high activity in the metathesis of cis-4-nonene. The results of metathesis experiments are summarized in Table 1.

TABLE 1

| Substrate | Catalysts | mol % | TOF[d] | Time to equilibrium conversion |
|---|---|---|---|---|
| cis-4-nonene[a] | 2 | 0.02 | 280 | <60 min |
| 1-nonene[b] | 2 | 0.1 | 13 | 66% conversion after 8 h |
| ethyl oleate[c] | 2 | 0.2 | 44 | <3 h |
| ethyl oleate[c] | 2 | 0.05 | 143 | 46% conversion after 4 h |
| cis-4-nonene[a] | 4 | 0.03 | 308 | <60 min |
| cis-4-nonene[a] | 6 | 0.02 | 325 | 10 min |
| cis-4-nonene[a] | 6 | 0.005 | 356 | 5 h |
| 1-nonene[b] | 6 | 0.05 | 133 | 6 h |
| ethyl oleate[c] | 6 | 0.1 | 5 | 42% conversion after 24 h |

[a]0.8M solution of cis-non-4-ene in toluene containing heptane as internal standard (0.1M).
[b]0.8M solution of 1-nonene in toluene containing heptane as internal standard (0.1M).
[c]0.5M solution of ethyl oleate in toluene containing octadecane as internal standard (0.1M).
[d]TOF at 3 min is in min$^{-1}$ and defined as the number of new alkenes produced per mol of W in the catalyst per min.

In general, the term "turnover frequency (TOF)" defines the number of turnovers of moles of olefin per time unit of a certain catalyst.

Example 5

Catalyst Reusing

Step a: A 0.8 M solution of cis-non-4-ene in toluene containing heptane as internal standard (0.1 M) was added to the catalyst prepared in Example 1 (catalyst to substrate ratio 1000) in a conical base vial containing a wing shaped magnetic stirrer.

Step b: The reaction mixture was stirred at 600 rpm and kept at 30° C. using an aluminum heating block for 20 min, sampling reaction mixture after 3 and 20 minutes. After leaving the supported catalyst settling, the olefin mixture was filtered out, and replaced by the same amount of fresh cis-non-4-ene solution, keeping the catalyst to substrate ratio to 1000.

Step b was repeated four times without any noticeable loss of activity of the catalyst.

The invention claimed is:

1. A tungsten catalyst comprising $(\equiv SiO)_X W(=O)(=CR^1R^2)(R^3 \text{ or } R^4)_{2-x}(L)_z$, wherein $(\equiv SiO)_X$ is comprised in a solid support, wherein each of $R^1$ and $R^2$ is independently R, —OR, —SR, —N(R)$_2$, —OC(O)R, —SOR, —SO$_2$R$_1$, —SO$_2$N(R)$_2$, C(O)N(R)$_2$, —NRC(O)R, or —NRSO$_2$R;

each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms in- dependently selected from nitrogen, oxygen, or sulfur, or:

two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

$R^3$ and $R^4$ have independently the same meaning as $R^1$ and $R^2$; or tris($C_{1-20}$ alkyl)silyl, tris($C_{1-20}$ alkyl)silyloxy, tris($C_{1-20}$ alkoxy)silyl, tris($C_{1-20}$ alkoxy)silyloxy, tris(aryl)silyl, tris(aryl)silyloxy, tris(aryloxy)silyl, or tris(aryloxy)silyloxy; and wherein x=1 or 2;

z=0, 1 or 2 or a number between 0 and 2;

and L is a neutral ligand.

2. A tungsten catalyst comprising $(\equiv SiO)_X W(=O)(=CR^1R^2)(R^3 \text{ or } R^4)_{2-x}(L)_z$, wherein $(\equiv SiO)_X$ is comprised in a solid support, wherein each of $R^1$ and $R^2$ is independently R, —OR, —SR, —N(R)$_2$, —OC(O)R, —SOR, —SO$_2$R, —SO$_2$N(R)$_2$, C(O)N(R)$_2$, —NRC(O)R, or —NRSO$_2$R;

each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms in- dependently selected from nitrogen, oxygen, or sulfur, or:

two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:

two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;

$R^3$ and $R^4$ have independently the same meaning as $R^1$ and $R^2$; or tris($C_{1-20}$ alkyl)silyl, tris($C_{1-20}$ alkyl)silyloxy, tris($C_{1-20}$ alkoxy)silyl, tris($C_{1-20}$ alkoxy)silyloxy, tris(aryl)silyl, tris(aryl)silyloxy, tris(aryloxy)silyl, or tris(aryloxy)silyloxy; and wherein x=1 or 2;

z=0, 1 or 2 or a number between 0 and 2;

and L is a neutral ligand, prepared according a method comprising at least the following step (i):

(i) reacting silica (SiO$_2$) with a tungsten oxo alkylidene complex comprising $(R^3)(R^4)W(=O)(=CR^1R^2)(L)_y$, wherein y=0, 1, or 2, wherein L, $R^1$, $R^2$, $R^3$ and $R^4$ have the meaning as defined above, and wherein $R^3$ and $R^4$ additionally may independently be Cl.

3. A method of forming an olefin from a first olefin and a second olefin in a metathesis reaction, comprising step (i):

(i) reacting the first olefin with the second olefin in the presence of the catalyst of claim 1.

4. The method of claim 3, wherein (a) the first olefin has a terminal olefinic double bond, and the second olefin has a terminal olefinic double bond, wherein the first and the second olefin are identical [homo or self-metathesis (SM)]; or (b) the first and the second olefin are different from one another [cross metathesis (CM)]; or (c) the first olefin has an internal olefinic double bond and the second olefin is ethylene [ethenolysis]; or (d) the first olefin is a cyclic olefin and the second olefin is a cyclic olefin, wherein the first and the second olefin may be identical or may be different from one another [cross metathesis (CM)]; or (e) the first olefin is a diene and the second olefin is a diene, wherein the first olefin and the second olefin are identical, wherein step (i) results in ring closing of the diene [ring closing metathesis (RCM)]; or (f) the first olefin is a cyclic olefin and the second olefin is a cyclic olefin, wherein the first olefin and the second olefin are identical, wherein step (i) results in a ring opening metathesis polymerization (ROMP); or (g) the first olefin is a cyclic olefin and the second olefin is a cyclic olefin, wherein the first olefin and the second olefin are identical, wherein step (i) results in a ring opening metathesis followed by a ring-closing metathesis reaction (ROM-RCM); or (h) the first olefin is a terminal diene and the second olefin is a terminal diene, wherein the first olefin and the second olefin are identical, and wherein step (i) results in an acyclic diene metathesis polymerization (AD-MET), wherein a polyene and ethylene are generated.

5. The method of claim 3, further comprising at least step (ii) or steps (ii) and (iii):
(ii) separating the catalyst from the reaction mixture obtained in step (i), by filtration, centrifugation, or distillation;
(iii) re-using the catalyst obtained in step (ii).

6. The tungsten catalyst of claim 1, wherein $=CR^1R^2$ is selected from $=CHC(CH_3)_3$ or $=CHC(CH_3)_2C_6H_5$.

7. The tungsten catalyst of claim 1, wherein $R^3$ and $R^4$ are independently pyrrol-1-yl, 2,5-dimethylpyrrol-1-yl, 2,5-diphenylpyrrol-1-yl, or —OR, wherein R is a six membered or 10 membered aryl ring.

8. The tungsten catalyst of claim 7, wherein R is a phenyl ring or an annelated phenyl ring substituted with one or more of: $C_{1-4}$ alkyl, $C_{1-4}$ alkoxy, optionally substituted phenyl, optionally substituted phenoxy, halogen.

9. The tungsten catalyst of claim 1, wherein $=CR^1R^2$ is selected from $=CHC(CH_3)_3$ or $=CHC(CH_3)_2C_6H_5$ and wherein $R^3=R^4=$—OR, wherein R is a phenyl ring or an annelated phenyl ring substituted with one or more of: $C_{1-4}$ alkyl, $C_{1-4}$ alkoxy, optionally substituted phenyl, optionally substituted phenoxy, halogen;
or
wherein $=CR^1R^2$ is selected from $=CHC(CH_3)_3$ or $=CHC(CH_3)_2C_6H_5$ and wherein $R^3=$—OR, wherein R is a phenyl ring or an annelated phenyl ring substituted with one or more of: $C_{1-4}$ alkyl, $C_{1-4}$ alkoxy, optionally substituted phenyl, optionally substituted phenoxy, halogen; and $R^4=$pyrrol-1-yl, 2,5-dimethylpyrrol-1-yl, or 2,5-diphenylpyrrol-1-yl;
or
wherein $=CR^1R^2$ is selected from $=CHC(CH_3)_3$ or $=CH(C(CH_3)_2C_6H_5$ and $R^3=R^4=$pyrrol-1-yl, 2,5-dimethylpyrrol-1-yl, or 2,5-diphenylpyrrol-1-yl.

10. The tungsten catalyst of claim 2, wherein in step (i) $SiO_{2-(700)}$ is reacted with $(ArO)_2W(=O)(=CHC(CH_3)_3)$ to yield $[(\equiv SiO)W(=O)(=CHC(CH_3)_3)OR]$ (Ar=2,6- dimesitylphenyl); or
wherein in step (i) $SiO_{2-(700)}$ is reacted with (ArO)(Me$_2$py)W(=O)(=CHtBu) to yield $[(\equiv SiO)W(=O)(=CHtBu)(Me_2py)]$ (Ar=2,6-dimesitylphenyl); Me$_2$py=2,5-dimethylpyrrol-1-yl); or
wherein in step (i) $SiO_{2-(700)}$ is reacted with (ArO)(Ph$_2$py)W(=O)(=CHtBu) to yield $[(\equiv SiO)W(=O)(=CHtBu)(Ph_{2py})]$ (Ar=2,6-dimesitylphenyl); Ph$_2$py=2,5-diphenylpyrrol-1-yl).

11. The tungsten catalyst of claim 1, wherein the solid support further comprises $Al_2O_3$, $ZrO_2$, $TiO_2$, $V_2O_5$, $MoO_2$, $WO_3$, a silicate, a zeolite, a sulfate of an alkali metal, a phosphate of an alkali metal, a sulfate of an earth alkali metal, or a phosphate of an earth alkali metal.

12. The tungsten catalyst of claim 2, wherein the solid support further comprises $Al_2O_3$, $ZrO_2$, $TiO_2$, $V_2O_5$, $MoO_2$, $WO_3$, a silicate, a zeolite, a sulfate of an alkali metal, a phosphate of an alkali metal, a sulfate of an earth alkali metal, or a phosphate of an earth alkali metal.

13. A method of making the tungsten catalyst of claim 1, comprising at least the following step (i):
(i) reacting silica (SiO$_2$) comprised in the solid support with a tungsten oxo alkylidene complex comprising $(R^3)(R^4)W(=O)(=CR^1R^2)(L)_y$, wherein y=0, 1 or 2, wherein each of $R^1$ and $R^2$ is independently R, —OR, —SR, —N(R)$_2$,—OC(O)R, —SOR, —SO$_2$R, —SO$_2$N(R)$_2$, C(O)N(R)$_2$, —NRC(O)R, or —NRSO$_2$R;
each R is independently hydrogen or an optionally substituted group selected from $C_{1-20}$ aliphatic, $C_{1-20}$ heteroalishatic having 1-3 heteroatoms independently selected from nitrogen, oxygen, or sulfur, phenyl, ferrocene, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms in- dependently selected from nitrogen, oxygen, or sulfur, or:
two R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur; or:
two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;
$R^3$ and $R^4$ have independently the same meaning as $R^1$ and $R^2$, or halogen, or tris($C_{1-20}$ alkyl)silyl, tris($C_{1-20}$ alkyl)silyloxy, tris($C_{1-20}$ alkoxy)silyl, tris($C_{1-20}$ alkoxy)silyoxy, tris(aryl)silyl, tris(aryl)silyloxy, tris(aryloxy)silyl, or tris(aryloxy)silyloxy; and
L is a neutral ligand.

14. The method of claim 13, comprising at least step (0.1) prior to step (i):
(0.1) heating the silica or heating the silica in vacuo.

15. The method of claim 13, wherein the silica comprises $SiO_{2-(700)}$.

16. The method of claim 13, wherein the tungsten oxo alkylidene complex used in step (i) is of formula

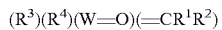

wherein
each of $R^3$ and $R^4$ has independently the meaning of R or —OR or —N(R)$_2$ or halogen;
and the resulting tungsten catalyst comprises

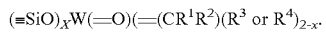

17. The method of claim 13, wherein $=CR^1R^2$ is selected from $=CHC(CH_3)_3$ or $=CHC(CH_3)_2C_6H_5$.

* * * * *

UNITED STATES PATENT AND TRADEMARK OFFICE
CERTIFICATE OF CORRECTION

PATENT NO. : 10,427,146 B2
APPLICATION NO. : 15/023892
DATED : October 1, 2019
INVENTOR(S) : Frater et al.

Page 1 of 1

It is certified that error appears in the above-identified patent and that said Letters Patent is hereby corrected as shown below:

In the Claims

Column 17, Line 46 reads, ". . . heteroatoms in- dependently . . ." which should read, ". . . heteroatoms independently . . ."

Column 18, Line 22 reads, ". . . heteroatoms in- dependently . . ." which should read, ". . . heteroatoms independently . . ."

Column 17, Line 46 reads, ". . . prepared according a method . . ." which should read, ". . . prepared according to a method . . ."

Column 20, Line 18 reads, ". . . heteroalishatic having 1-3 . . ." which should read, ". . . heteroaliphatic having 1-3 . . ."

Column 20, Line 33 reads, ". . . in- dependently selected . . ." which should read, ". . . independently selected . . ."

Column 20, Line 51 reads, ". . . alkoxy)silyoxy . . ." which should read, ". . . alkoxy)silyloxy. . ."

Signed and Sealed this
Fourteenth Day of April, 2020

Andrei Iancu
*Director of the United States Patent and Trademark Office*